United States Patent
DeBusk et al.

(10) Patent No.: US 9,700,462 B2
(45) Date of Patent: Jul. 11, 2017

(54) SYSTEM FOR MONITORING AND CONTROLLING NEGATIVE PRESSURE WOUND THERAPY

(71) Applicant: DeRoyal Industries, Inc., Powell, TN (US)

(72) Inventors: Brian C. DeBusk, Knoxville, TN (US); Timothy A. Alleman, Knoxville, TN (US); Nephi Zufelt, Knoxville, TN (US); Greg Hodge, Knoxville, TN (US)

(73) Assignee: DeRoyal Industries, Inc., Powell, TN (US)

( * ) Notice: Subject to any disclaimer, the term of this patent is extended or adjusted under 35 U.S.C. 154(b) by 417 days.

(21) Appl. No.: 14/541,425

(22) Filed: Nov. 14, 2014

(65) Prior Publication Data
US 2015/0133829 A1    May 14, 2015

Related U.S. Application Data

(60) Provisional application No. 61/904,014, filed on Nov. 14, 2013.

(51) Int. Cl.
*G08B 1/08* (2006.01)
*A61F 13/00* (2006.01)
*A61M 1/00* (2006.01)

(52) U.S. Cl.
CPC ..... *A61F 13/00068* (2013.01); *A61M 1/0035* (2014.02); *A61M 1/0088* (2013.01);
(Continued)

(58) Field of Classification Search
CPC .... A61F 13/00068; A61F 13/00; A61F 13/02; A61M 1/00; A61M 27/00
(Continued)

(56) References Cited

U.S. PATENT DOCUMENTS

| | | |
|---|---|---|
| 4,969,880 A | 11/1990 | Zamierowski |
| 5,100,396 A | 3/1992 | Zamierowski |

(Continued)

OTHER PUBLICATIONS

International Search Report and Written Opinion, PCT/US2014/065680, date of mailing May 14, 2015—31 pages.

*Primary Examiner* — Toan N Pham
(74) *Attorney, Agent, or Firm* — Luedeka Neely Group PC

(57) ABSTRACT

A system for monitoring and controlling negative pressure wound therapy includes a microcontroller that controls means for maintaining reduced air pressure based on a pressure signal from a pressure sensor. The means for maintaining reduced air pressure may include a vacuum pump and valve. The system includes a mobile communication device having a microprocessor, touchscreen display, data storage device, GPS module, and wireless transceiver. The microprocessor generates control signals sent to the microcontroller to control the means for maintaining reduced air pressure to provide continuous or intermittent reduced air pressure. The microprocessor monitors the pressure signal and generates a closed-system alarm, leak-detected alarm or open-system alarm. The closed-system alarm indicates an air pressure leak rate below a closed-system threshold. The leak-detected alarm indicates an air pressure leak rate above a leak-detected threshold and below an open-system threshold. The open-system alarm indicates an air pressure leak rate above the open-system threshold.

31 Claims, 13 Drawing Sheets

(52) U.S. Cl.
CPC ....... *A61M 1/0037* (2013.01); *A61M 2205/15* (2013.01); *A61M 2205/18* (2013.01); *A61M 2205/3334* (2013.01); *A61M 2205/3344* (2013.01); *A61M 2205/3389* (2013.01); *A61M 2205/3553* (2013.01); *A61M 2205/3584* (2013.01); *A61M 2205/3592* (2013.01); *A61M 2205/505* (2013.01)

(58) Field of Classification Search
USPC ........ 340/539.12; 602/42, 46; 604/319, 543; 128/897
See application file for complete search history.

(56) References Cited

U.S. PATENT DOCUMENTS

| | | |
|---|---|---|
| 5,261,893 A | 11/1993 | Zamierowski |
| D364,679 S | 11/1995 | Heaton et al. |
| 5,527,293 A | 6/1996 | Zamierowski |
| 5,636,643 A | 6/1997 | Argenta et al. |
| 5,645,081 A | 7/1997 | Argenta et al. |
| 6,071,267 A | 6/2000 | Zamierowski |
| 6,936,037 B2 | 8/2005 | Bubb et al. |
| 7,216,651 B2* | 5/2007 | Argenta .............. A61F 13/0246 128/897 |
| 2007/0118096 A1* | 5/2007 | Smith .................... A61B 5/445 604/541 |
| 2008/0030345 A1 | 2/2008 | Austin et al. |
| 2009/0043268 A1 | 2/2009 | Eddy et al. |
| 2009/0326488 A1 | 12/2009 | Budig et al. |
| 2010/0022990 A1 | 1/2010 | Karpowicz et al. |
| 2011/0092958 A1* | 4/2011 | Jacobs ................ A61M 1/0031 604/543 |
| 2011/0213287 A1* | 9/2011 | Lattimore ......... A61F 13/00021 602/46 |
| 2015/0025482 A1 | 1/2015 | Begin et al. |

* cited by examiner

| Command Message | Command Message Format | Response Message | Comments |
|---|---|---|---|
| Locate Unit | $<strCellularPassword>\|Locate\n | $<strTime>\|$<strLocation>\n | Used to locate NPWT unit |
| Ping Unit (play sound) | $<strCellularPassword>\|Ping\n | $<strTime>\|$<strLocation>\n | Makes NPWT unit repeatedly play "Ping" sound at maximum volume |
| Service Lock | $<strCellularPassword>\|Service Lock\n | $<strTime>\|$<strLocation>\n | Deactivates any therapy and forces the entry of the Service lock code before the NPWT unit will re-activate. This should also persist through power-off and/or the loss of power. |
| Factory Lock | $<strCellularPassword>\|Factory Lock\n | $<strTime>\|$<strLocation>\n | Deactivates any therapy and forces the entry of the Factory lock code before the NPWT unit will re-activate. This should also persist through power-off and/or the loss of power. |
| Service Remote Unlock | $<strCellularPassword>\|Service Unlock\|$<strServiceCode>\n | | Unlocks a Service Lock |
| Factory Remote Unlock | $<strCellularPassword>\|Factory Unlock\|$<strFactoryCode>\n | | Unlocks a Factory Lock |
| Download log after time $<parmTime> | $<strCellularPassword>\|Log=$<parmTime>\n | $<strTime>\|$<strLocation>\|Start Log\|<lines from persistent storage where timestamp is after $paramTime\|Stop Log\n | Prevents downloading too much information |
| Operating Status | $<strCellularPassword>\|Status\n | $<strtime>\|$<strLocation>\|Off\|$<tElapsedTime>\n $<strtime>\|$<strLocation>\|Continuous\|$<strContPressure>\|$<tElapsedTime>\n $<strtime>\|$<strLocation>\|Intermittent\|$<iVarPressureHigh>\|$<iVarPressureLow>\|$<iVarInterval>\|$<tElapsedTime>\n $<strTime>\|$<strLocation>\|Alarm-alarm name>\|$<tAlarmTime>\|$<tAlarmElapsedTime>\n | One of these codes can be returned, but no more than one |
| Resume Last Therapy | $<strCellularPassword>\|Resume\n | $<strTime>\|$<strLocation>\n | |
| Set Parameter <Variable> | $<strCellularPassword>\|Set\|<Variable>\|<Value>\n | $<strTime>\|$<strLocation>\n | The NPWT unit uses a Set/Get protocol to set variables |
| Get Parameter <Variable> | $<strCellularPassword>\|Get\|<Variable>\n | $<strTime>\|$<strLocation>\|<Variable>\|<Value>\n | Could be addressed by their names on the "Variable" tab |
| Activate Continuous Mode | $<strCellularPassword>\|Activate Continuous\n | $<strTime>\|$<strLocation>\n | |
| Activate Intermittent Mode | $<strCellularPassword>\|Activate Intermittent\n | $<strTime>\|$<strLocation>\n | |
| Stop Unit | $<strCellularPassword>\|Stop\n | $<strTime>\|$<strLocation>\n | |
| Reload Default Values | $<strCellularPassword>\|Reload Defaults\n | $<strTime>\|$<strLocation>\n | |
| Self Diagnostic | $<strCellularPassword>\|Self Diagnose\n | $<strTime>\|$<strLocation>\|<diagnostics string>\n | The diagnostics string is provided by the embedded controller |
| Leak Trend | $<strCellularPassword>\|Leak Trend\n | $<strTime>\|$<strLocation>\|<leak trend string>\n | This is a calculation by the controller to predict the life of the disposable dressing |

*FIG. 10*

| Global Variables on Mobile Communication Device (persistent across multiple states and power loss) | | | |
|---|---|---|---|
| Variable Name | Type | Description | Data Range |
| iContPressure | Int 16 | Pressure setting for continuous therapy | -10 to -200 mmHG |
| iVarPressureHigh | Int 16 | Pressure setting for high value of interval therapy | -10 to -200 mmHG |
| iVarPressureLow | Int 16 | Pressure setting for low value of interval therapy | -10 to -200 mmHG |
| iVarIntervalHigh | Int 16 | Time setting for high value of interval therapy | 3 seconds to 60 minutes |
| iVarIntervalLow | Int 16 | Time setting for low value of interval therapy | 3 seconds to 60 minutes |
| iLastTherapyMode | Int 16 | Stores last therapy mode (used for "Resume" function) | 0=none; 1=Continuous; 2 = Intermittent |
| strLanguage | Char 32 | Language (text) for messages and buttons | English, Spanish, German, French, Dutch |
| bLocked | Boolean | When true, the unit's settings are locked-out to the end-user (i.e. changing pressures) | true, false |
| tLockTime | Time | Sets the auto-timer to lock the unit after therapy is started (continuous or intermittent) | 10 seconds to 60 minutes |
| bServiceLocked | Boolean | When true, unit will wait until a Service (or Factory) code is entered before further action | true, false |
| bFactoryLocked | Boolean | When true, unit will wait until a Factory code is entered before further action | true, false |
| iScreenBlankTime | Int 16 | Timer (in seconds) before blanking display screen | 0 (never) to 999 seconds |
| tElapsedTime | Time | Time elapsed since the start of therapy (or since unit turned off) | 0 to 9999999 (largest time value) |
| tAlarmTime | Time | Time of last alarm | 0 to 9999999 (largest time value) |
| tAlarmElapsedTime | Time | Time elapsed since last alarm and time alarm was cleared | 0 to 9999999 (largest time value) |
| tAlarmVolume | Int 16 | Volume for alarms | 0 to 100 |
| tPlaybackVolume | Int 16 | Volume for non-alarm audio playback (i.e. Demonstration Videos) | 0 to 100 |
| bWirelessDisabled | Boolean | When true, the wireless transceiver is turned off | true, false |
| Local Variables in Mobile Communication Device Obtained through Embedded Controller | | | |
| iBatteryLevel | Int 16 | Battery (34) level expressed as % value | 0 to 100 |
| iLeakRate | Int 16 | Leakage rate of dressing measured in mmHg/hour | 0 to 32768 |
| Local Variables in Mobile Communication Device Obtained through Wireless Modem | | | |
| strTime | Char 32 | String used to timestamp key events | |
| strLocation | Char 32 | String used to identify unit's location | |

*FIG. 11*

Settings Maintained on Mobile Communication Device

| Setting Name | Type | Description | Data Range |
|---|---|---|---|
| iDefaultContPressure | Int 16 | Default pressure setting for continuous therapy | -10 to -200 mmHG |
| iDefaultVarPressureHigh | Int 16 | Default pressure setting for high level of intermittent therapy | -10 to -200 mmHG |
| iDefaultVarPressureLow | Int 16 | Default pressure setting for low level of intermittent therapy | -10 to -200 mmHG |
| iDefaultIntervalHigh | Int 16 | Default time setting for length of high period of intermittent therapy | 3 seconds to 60 minutes |
| iDefaultIntervalLow | Int 16 | Default time setting for length of low period of intermittent therapy | 3 seconds to 60 minutes |
| iDefaultScreenBlankTime | Int 16 | Default time setting before display screen is blanked | 0 (never) to 999 seconds |
| iLeakRateLimitLow | Int 16 | Low limit for dressing leakage rate (used to detect closed system) | 0 to 32768 |
| iLeakRateLimitHigh | Int 16 | High limit for dressing leakage rate (used to detect a leaking dressing) | 0 to 32768 |
| iLeakRateSystemOpen | Int 16 | High limit for determining if system is open (i.e. not connected to dressing) | 0 to 32768 |
| iBatteryLevelLimitLow | Int 16 | Low limit for battery indicator (used to trigger low battery alarm) | 0 to 100 |
| tDefaultLockTime | Time | Default time setting for auto-timer that locks unit after therapy is started | |
| strDeviceID | Char 32 | Unit ID assigned by NPWT service provider (factory setting - not modifiable by users or owners) | null-terminated string |
| strDevicePhoneNumber | Char 32 | Identifies the cellular phone number for mobile communication device | null-terminated string |
| strDestinationPhoneNumber | Char 32 | Identifies the cellular phone number for destination messages sent from mobile communication device | null-terminated string |
| strCellularPassword | Char 32 | Identifies the password used to modify parameters | null-terminated string |
| strDMEIdentifier | Char 32 | DME identifier used by NPWT service provider (factory setting - not modifiable by users or owners) | null-terminated string |
| strDMEName | Char 256 | DME name, which can be changed by owner (i.e. the DME or hospital who purchases the device) | null-terminated string |
| strDMEDeviceName | Char 256 | DME device name, for use by DME to identify the individual unit (changeable by owner) | null-terminated string |
| strServiceCode | Char 4 | Four-digit code used to enter service mode (changeable by owner) | |
| strFactoryCode | Char 4 | Four-digit code used to enter service & factory mode (factory setting - not changeable by owner) | |
| strLockCode | Char 4 | Four-digit code used to lock and unlock the unit (changeable by owner) | |

*FIG. 12*

| Serial commands sent by the mobile communication device to the embedded controller to start and stop therapy and do diagnostics | | | | | | |
|---|---|---|---|---|---|---|
| Mechanical Command | Description | Outbound Serial String (from handset to embedded controller) * | Reply (from embedded controller back to handset) | Comments | Example Output | Example Return Value |
| Power Up/Reset | Performs system check and initialization | "R=$<strTime>\n" | "S\n" on success and a "F=<text string>\n" upon failure | Simple power-on self tests for the embedded controller. This also uses the time string to set the controller's real-time clock. | "R\n" | "F=no battery detected\n" |
| Diagnostic Mode | Diagnoses pump, valve and pressure sensor | "D\n" | "S\n" on success and a "F=<text string>\n" upon failure | For use with a closed system. Runs pump and opens valves with a variety of pressure measurements. | "D\n" | "F=motor drive circuit open\n" |
| Leak Rate | Returns the dressing leakage rate in mmHg/hour | "L\n" | "S=dddd\n" or "F\n" if the unit is not in continuous or intermittent mode | dddd = leak rate in mmHg/hour expressed as a decimal-based integer number with no decimal point or decimal places | "L\n" | "S=33\n" |
| Battery Status | Returns the minutes of battery power remaining | "B\n" | "S=mmmm\n" or "F\n" upon failure | mmmm=int16 number of units (100 = full) of battery life remaining. | "B\n" | "S=75\n" |
| Stop | Stops pump | "S\n" | "S\n" on success and "F\n" on failure | Discontinues the PWM signal to the pump. Dressing vacuum will be maintained until the dressing seal is interrupted or disconnected | "S\n" | "S\n" |
| Emergency Stop | Stops pump, opens valve | "E\n" | "S\n" on success and "F\n" on failure | Discontinues the PWM signal and also opens the valve to atmospheric pressure. All dressing vacuum will be lost under this condition | "S\n" | "S\n" |
| Continuous Mode On | Puts embedded controller state into the continuous vacuum protocol | "C=$<iContPressure>\n" | "S\n" on success and "F\n" on failure | The one key parameter for continuous therapy is transmitted in this command | "C=125\n" | "S\n" |
| Intermittent Mode On | Puts embedded controller state into the intermittent vacuum protocol | "I=$<iVarPressureHigh>{ $<iVarPressureLow>{$<i VarIntervalHigh>{ $<iVarIntervalLow>\n" | "S\n" on success and "F\n" on failure | All four key parameters for intermittent therapy are transmitted in this command | "I=80,15,20 ,20\n" | "S\n" |

* Quotes are only used to delimit messages
The "\n" character denotes a line feed (ASCII integer value 13). A subsequent or preceding "\r" (ASCII integer value 10) is optional.
Variables are expressed as $<var name> in the message format

FIG. 13

Transition States

| Outgoing State | Incoming State | Log in Persistent Storage? | Send Outgoing Cellular Message? *** | Message to be Sent * |
|---|---|---|---|---|
| Power Off | Splash Screen | Yes | Yes | $<strTime>\|$<strLocation>\|Unit Startup\n |
| <any state> | Power Off | Yes | Yes | $<strTime>\|$<strLocation>\|Unit Shutdown\n |
| Continuous Mode Setup | Continuous Mode Active | Yes | Yes | $<strTime>\|$<strLocation>\|Continuous Mode On\|$<iContPressure>\n |
| Intermittent Mode Setup | Intermittent Mode Active | Yes | Yes | $<strTime>\|$<strLocation>\|Intermittent Mode On\|$<iVarPressureHigh>\|$<iVarPressureLow>\|$<iVarIntervalHigh>\|$<iVarIntervalLow>\n |
| Continuous Mode Active | Continuous Mode Setup | Yes | Yes | $<strTime>\|$<strLocation>\|Continuous Mode Off\n |
| Intermittent Mode Active | Intermittent Mode Setup | Yes | Yes | $<strTime>\|$<strLocation>\|Intermittent Mode Off\n |
| <any state> | Leak Detected Alarm | Yes | No | $<strTime>\|$<strLocation>\|Leak Detected\|$<iLeakRate>\|$<iLeakRateLimitHigh>\n |
| <any state> | Closed System Alarm | Yes | No | $<strTime>\|$<strLocation>\|Closed System\|$<iLeakRate>\|$<iLeakRateLimitLow>\n |
| <any state> | Open System Alarm | Yes | No | $<strTime>\|$<strLocation>\|Open System\|$<iLeakRate>\|$<iLeakRateSystemOpen>\n |
| <any state> | Battery Alarm | Yes | No | $<strTime>\|$<strLocation>\|Low Battery\|$<iBatteryLevel>\|$<iBatteryLevelLimitLow>\n |
| Leak Detected Alarm | <any state> | Yes | No | $<strTime>\|$<strLocation>\|Leak Cleared\n |
| Closed System Alarm | <any state> | Yes | No | $<strTime>\|$<strLocation>\|Closed System Cleared\n |
| Open System Alarm | <any state> | Yes | No | $<strTime>\|$<strLocation>\|Open System Cleared\n |
| Battery Alarm | <any state> | Yes | No | $<strTime>\|$<strLocation>\|Low Battery Cleared\n |
| Mode Selection -- Resume | Continuous Mode Active | Yes | No | $<strTime>\|$<strLocation>\|Continuous Mode On Resumed\|$<iContPressure>\n |
| Mode Selection -- Resume | Intermittent Mode Active | Yes | No | $<strTime>\|$<strLocation>\|Intermittent Mode On Resumed\|$<iVarPressureHigh>\|$<iVarPressureLow>\|$<iVarIntervalHigh>\|$<iVarIntervalLow>\n |
| Wireless | Wireless Mode Activated | Yes | Yes | $<strTime>\|$<strLocation>\|Wireless On\n |
| Wireless | Wireless Mode Deactivated | Yes | Yes | $<strTime>\|$<strLocation>\|Wireless Off\n |
| Service | Self-Diagnostic | Yes | No | $<strTime>\|$<strLocation>\|Self Diagnostic\|<text string>\n ** |
| Language | <specific language chosen> | Yes | No | $<strTime>\|$<strLocation>\|Language\|$<strLanguage>\n |
| User's Guide | Section <abc> Display | Yes | No | $<strTime>\|$<strLocation>\|User's Guide\|<section name>\n |
| User's Guide | Demo video <abc> Display | Yes | No | $<strTime>\|$<strLocation>\|Demo Video\|<video name>\n |
| User's Guide | Phone & Internet Support | Yes | No | $<strTime>\|$<strLocation>\|Phone & Internet Support\n |

* Variables are expressed as $<var name> in the message format.
** The self-diagnostic string is free-form text returned from the embedded controller.
*** "Send Outgoing Cellular Message" may be programmatically driven flags that are set by the application to control data usage.
Note: The NPWT unit preferably records every significant it encounters in persistent storage, but only sends cellular messages for the most important events.

FIG. 14

SYSTEM FOR MONITORING AND CONTROLLING NEGATIVE PRESSURE WOUND THERAPY

RELATED APPLICATIONS

This application claims priority to provisional patent application Ser. No. 61/904,014, filed Nov. 14, 2013, titled "SYSTEM FOR MONITORING AND CONTROLLING NEGATIVE PRESSURE WOUND THERAPY," the entire contents of which are incorporated herein by reference.

FIELD

This invention relates to controlling and monitoring medical devices. More particularly, this invention relates to a system for controlling and monitoring the application of negative pressure therapy to a wound.

BACKGROUND

Negative-pressure wound therapy (NPWT) is a therapeutic technique wherein a vacuum dressing is applied to a wound to promote and enhance healing. NPWT involves the controlled application of sub-atmospheric pressure to an airspace over a wound using a sealed wound dressing connected to a vacuum pump. The sub-atmospheric pressure (also referred to herein as "negative pressure") draws fluid out of the wound and increases blood flow to the area. The vacuum may be applied continuously or intermittently, depending on the type of wound being treated and the clinical objectives. Dressings used in NPWT include gauze and open-cell foam dressings sealed with a suction dome that contains the vacuum at the wound site. Most NPWT devices provide for intermittent removal of fluid drained from the wound bed.

In most NPWT systems, a non-adherent dressing film covers the wound, a second dressing or filler material is fitted to the contours of the wound, and a suction dome or transparent film is applied to seal the airspace over the wound. One end of a vacuum tube is connected to an opening in the suction dome or film and the other end of the vacuum tube is connected to a canister and a vacuum pump. Excess fluid is removed from the wound through the vacuum tube to enhance circulation, create a moist healing environment, and reduce edema.

Typically, an NPWT device is prescribed by healthcare professionals for ongoing treatment of a patient's wound after the patient has been discharged from a hospital. After the patient is discharged, it becomes more difficult for healthcare providers to confirm that the NPWT device is functioning properly and that the patient is using the device in a proper manner. Generally, frequent in-home visits by healthcare providers are needed to check the progress of wound healing and confirm proper operation and use of the NPWT device.

The cost of NPWT devices is typically covered by Medicare or other healthcare insurance. In the Medicare domain, use of an NPWT device within a hospital is covered by Medicare Part A. Once a patient is discharged from the hospital, the cost of the NPWT device may be reimbursed under Medicare Part B. Keeping up with the Medicare Part A to Part B transition and ensuring that costs are reimbursed under the proper Medicare regime can be an onerous task for healthcare administrators.

What is needed, therefore, is a system for remotely monitoring the location and operational status of a NWPT device, for remotely controlling its operation, for remotely confirming that the device is being used properly to provide the needed therapy, and for updating insurance reimbursement conditions.

SUMMARY

The above and other needs are met by a system for monitoring and controlling negative pressure wound therapy for treating a wound on a person's body. In a preferred embodiment, the system includes means for maintaining reduced air pressure in an airspace over the wound, a pressure sensor, a microcontroller, and a mobile communication device. The pressure sensor senses air pressure and generates a pressure signal based on sensed air pressure, and the microcontroller controls the means for maintaining reduced air pressure based on the pressure signal. The means for maintaining reduced air pressure may include a vacuum pump and a valve.

The mobile communication device includes a microprocessor in electrical communication with the microcontroller, a touchscreen display, a data storage device, a GPS module, and a wireless transceiver. The microprocessor executes software instructions to generate control signals that are provided to the microcontroller to control the means for maintaining reduced air pressure to maintain either a continuous reduced air pressure state or an intermittent reduced air pressure state in the airspace over the wound. The microprocessor also executes software instructions to monitor the pressure signal and generate a closed-system alarm, a leak-detected alarm or an open-system alarm. The closed-system alarm is generated if the pressure signal indicates an air pressure leak rate that is below a closed-system threshold. The leak-detected alarm is generated if the pressure signal indicates an air pressure leak rate that is above a leak-detected threshold and below an open-system threshold. The open-system alarm is generated if the pressure signal indicates an air pressure leak rate that is above the open-system threshold.

In some embodiments, the system includes a NPWT service provider computer in communication with the wireless transceiver of the mobile communication device via a communication network. The NPWT service provider computer is also in communication with a healthcare provider computer via the communication network. The wireless transceiver transmits one or more of the pressure signal, the open-system alarm, the leak-detected alarm, and the closed-system alarm to the NPWT service provider computer via the communication network, and the NPWT service provider computer sends a corresponding alert communication to the healthcare provider computer via the communication network.

In some embodiments, a first housing encloses the means for maintaining reduced air pressure and the microcontroller. The first housing has a recess in one of its outer surfaces. A second housing that encloses the mobile communications device is sized to fit substantially within the recess in the outer surface of the first housing.

In some embodiments, there is a hinged connection between the first housing and the second housing, such that the second housing is rotatable on the hinged connection to move from a first position to a second position. In the first position, an outer surface of the second housing is substantially flush with the outer surface of the first housing. In the second position, the outer surface of the second housing is tilted with respect to the outer surface of the first housing.

In some embodiments, a power source is disposed in the first housing for providing power to the means for maintaining reduced air pressure. A tether harness is connected between the first housing and the second housing through which the mobile communication device in the second housing is electrically connected to the microcontroller in the first housing.

In some embodiments, the system includes a canister for receiving fluid drained from the wound, and a fluid sensor that is electrically connected to the microcontroller. The fluid sensor senses a quantity of fluid in the canister and generates a fluid signal based thereon, and the microcontroller controls the means for maintaining reduced air pressure based on the fluid signal.

Various embodiments of the system include a NPWT service provider computer that is in communication with the wireless transceiver of the mobile communication device via the communication network. The NPWT service provider computer is also in communication with a healthcare provider computer via the communication network.

In some embodiments, the microprocessor of the mobile communication device generates a canister filling rate signal based on the fluid signal. The wireless transceiver transmits the canister filling rate signal to the NPWT service provider computer via the communication network, and the NPWT service provider computer sends an alert communication based on the canister filling rate signal to the healthcare provider computer via the communication network.

In some embodiments, the wireless transceiver transmits one or more of the pressure signal, the open-system alarm, the leak-detected alarm, and the closed-system alarm to the NPWT service provider computer via the communication network. The NPWT service provider computer then sends an alert communication based on these signals or alarms to the healthcare provider computer via the communication network.

In some embodiments, the GPS module of the mobile communication device generates location coordinate information indicative of the geographic location of the mobile communication device. The microprocessor determines whether the location coordinate information indicates that the mobile communication device has moved from inside to outside a geofence boundary and generates a geofence alert message based thereon. The wireless transceiver transmits the geofence alert message to the NPWT service provider computer via the communication network. The NPWT service provider computer then sends a geofence alert communication based on the geofence alert message to the healthcare provider computer via the communication network.

In some embodiments, the NPWT service provider computer generates a pressure-setting command message and transmits the pressure-setting command message to the mobile communication device via the communication network. The wireless transceiver receives the pressure-setting command message and the microprocessor executes software instructions to generate control signals based on the pressure-setting command message. The control signals are then provided to the microcontroller to control the means for maintaining reduced air pressure to maintain a reduced air pressure in the airspace over the wound.

In some embodiments, the GPS module of the mobile communication device determines a geographic location of the mobile communication device after the patient whose wound is being treated has been discharged from a healthcare facility. The microprocessor of the mobile communication device generates a location message based on the geographic location. The wireless transceiver of the mobile communication device transmits the location message to the NPWT service provider computer via the communication network. The NPWT service provider computer then provides patient location information via the communication network to a mobile device carried by a healthcare provider. The patient location information indicates to the healthcare provider the location at which to find the patient whose wound is being treated.

In some embodiments, the data storage device of the mobile communication device stores a unit ID number that uniquely identifies the mobile communication device. The NPWT service provider computer of this embodiment receives patient identification information from the healthcare provider computer that identifies the patient being treated by the system. The microprocessor of the mobile communication device generates a message that includes the unit ID number, and the wireless transceiver transmits the message to the NPWT service provider computer via the communication network. The NPWT service provider computer then associates the unit ID number transmitted from the mobile communication device with the patient identification information sent from the healthcare provider computer in a database connected to the NPWT service provider computer.

In some embodiments, the data storage device of the mobile communication device stores electronic documentation of standard practices that law requires medical device suppliers to abide by and to disclose to patients being treated by the system. The touchscreen displays the standard practices for viewing by the patient, and receives an indication from the patient confirming that the patient has viewed the standard practices. The wireless transceiver then transmits the indication to the NPWT service provider computer via the communication network.

In some embodiments, the data storage device stores information regarding characteristics of the wound and treatment of the wound. The touchscreen displays the information regarding characteristics of the wound and treatment of the wound for viewing by a healthcare provider attending to the patient. The touchscreen also receives information from the healthcare provider regarding characteristics of the wound and treatment of the wound provided to the patient by the healthcare provider. The wireless transceiver then transmits the information regarding characteristics of the wound and treatment of the wound to the NPWT service provider computer via the communication network.

In some embodiments, the touchscreen displays a prompt for viewing by a healthcare provider, where the prompt requests input regarding whether use of the system for treatment of the person's wound is covered by a particular type of healthcare insurance, such as Medicare Part A or B. The touchscreen receives information input by the healthcare provider in response to the prompt. The wireless transceiver then transmits the information input by the healthcare provider to the NPWT service provider computer via the communication network.

BRIEF DESCRIPTION OF THE DRAWINGS

Other embodiments of the invention will become apparent by reference to the detailed description in conjunction with the figures, wherein elements are not to scale so as to more clearly show the details, wherein like reference numbers indicate like elements throughout the several views, and wherein:

FIG. 10 depicts command and response message formats used in a negative pressure wound therapy system according to an embodiment of the invention;

FIG. 11 depicts global and local variables used in a negative pressure wound therapy unit according to an embodiment of the invention;

FIG. 12 depicts settings maintained in a negative pressure wound therapy unit according to an embodiment of the invention;

FIG. 13 depicts various commands used by a negative pressure wound therapy unit to control the starting and stopping of therapy and to do diagnostics according to an embodiment of the invention; and FIG. 14 depicts transition states implemented in a negative pressure wound therapy system according to an embodiment of the invention.

DETAILED DESCRIPTION

Some embodiments described herein are directed to a negative pressure wound therapy (NPWT) system, which is one example of an item of Durable Medical Equipment (DME). DME is typically dispensed to a patient to treat a particular type of medical condition, which treatment may begin in a hospital setting and continue in a home healthcare setting after the patient leaves the hospital. Those skilled in the art will appreciate that various aspects of the invention described herein are not limited to NPWT systems, but are applicable as well to other types of DME.

Figure 1:
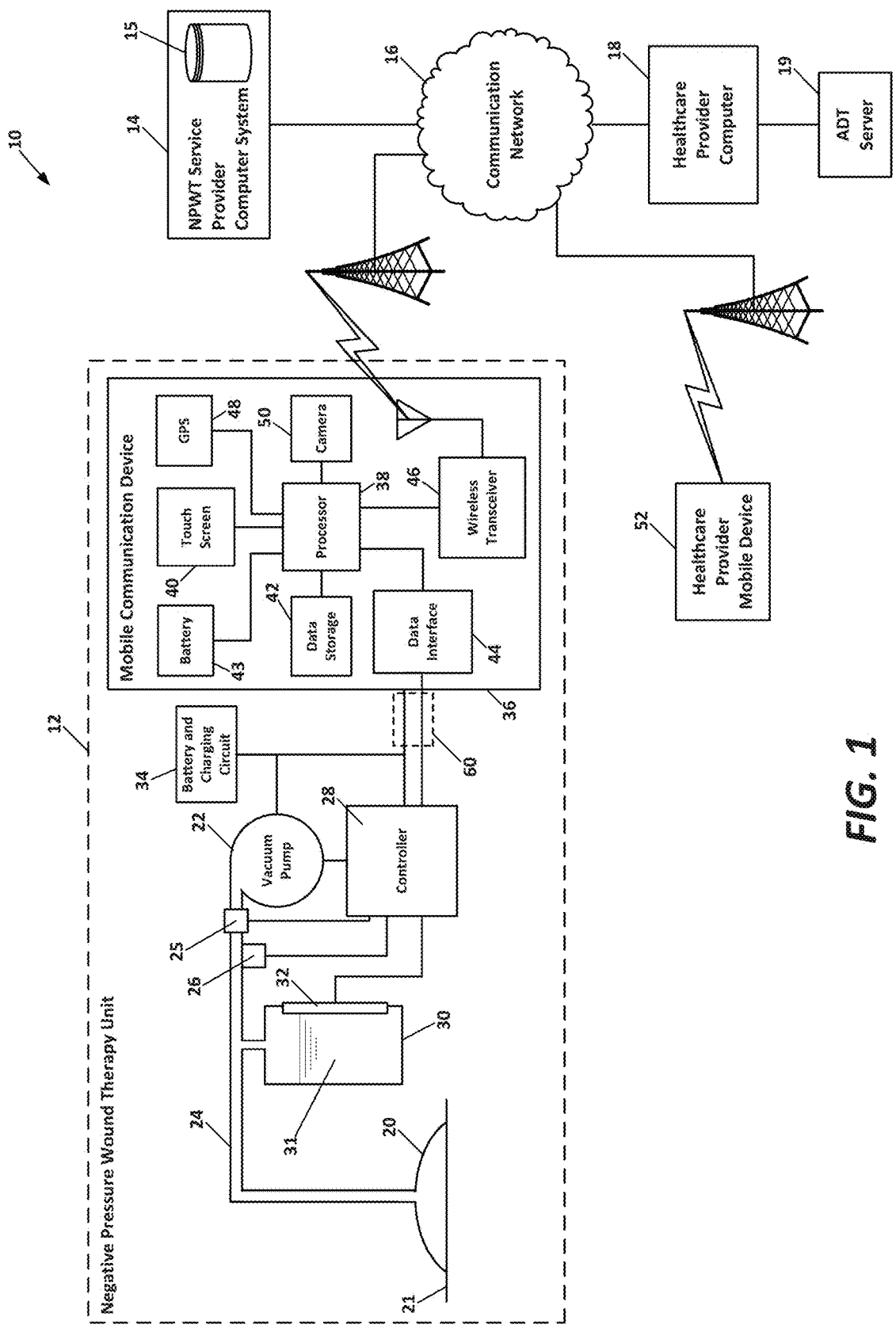
FIG. 1 depicts a block diagram of a system for monitoring and controlling a negative pressure wound therapy unit according to an embodiment of the invention.

As shown in FIG. 1, a preferred embodiment of an NPWT system 10 includes an NPWT unit 12 and an NPWT service provider computer system 14. The NPWT service provider computer system 14 is in communication with the NPWT unit 12 and with a healthcare provider computer 18 via a communication network 16, such as the Internet.

The healthcare provider computer 18 may be, for example, a desktop computer, laptop computer, tablet computer, or smart phone. A browser application is loaded on the healthcare provider computer 18 to provide access to an NPWT service provider website via the communication network 16.

The healthcare provider computer 18 is also in communication with an admissions-discharge-transfer (ADT) server 19. The ADT server 19 comprises one or more computers that store and manage records regarding the status of patients receiving treatment in a medical facility. Generally, a patient's status is either admitted to the facility, discharged from the facility, or transferred to another facility. Communication between the healthcare provider computer 18 and the ADT server 19 may be through the communication network 16 or through a local area network (LAN).

With continued reference to FIG. 1, the NPWT service provider computer system 14 comprises one or more computers that store information and execute software for monitoring and controlling multiple NPWT units 12. As the term is used herein, an "NPWT service provider" may be a company that supplies NPWT units to healthcare providers for use in treating wounds and that monitors and controls NPWT units on behalf of the healthcare providers. An example of one such NPWT service provider is DeRoyal Industries, Inc. of Powell, Tenn.

The NPWT service provider computer system 14 preferably includes an NPWT unit database 15 that stores information regarding NPWT units. For each NPWT unit, the database 15 associates the unit's unique ID number, the identity of the healthcare provider entity that obtained the unit from the service provider, the identity of the patient to which the unit has been dispensed, the current location of the unit (preferably based on GPS data, cellular data, Wi-Fi data, or a combination thereof), current status of the unit (active or inactive), the current operational mode (continuous or intermittent pressure), a log of alert communications that have been received from the unit, a log of command communications sent to the unit, and an insurance reimbursement indicator for the unit (private insurance or Medicare Part A or B). The information stored in the NPWT unit database 15 provides a complete chain of custody for each NPWT unit 12, including transfer of the unit from the DME service provider to the hospital, dispensing to a patient, leaving the hospital with the patient, use in the patient's home, transfer back to the hospital or DME service provider, and so forth.

In a preferred embodiment, the NPWT unit 12 comprises a vacuum pump 22 that pulls a vacuum on an air line 24. The level of air pressure in the air line 24 is determined by a valve 25 and is sensed by a pressure sensor 26. The pump 22 and valve 25 are preferably powered by a Lithium-ion or Lithium-polymer battery pack and charging circuit 34. The end of the air line 24 opposite the pump/valve is connected to a suction dome 20 that is sealed over a wound on a person's body 21. Fluid 31 from the wound flows through the air line 24 and into a collection canister 30. The level of fluid 31 in the canister 30 is sensed by a fluid level sensor 32.

A microcontroller 28 receives a fluid level sensor signal from the fluid level sensor 32 and an air pressure signal from the pressure sensor 26. Based on these signals and received command/control messages described hereinafter, the microcontroller 28 controls the pump 22 and valve 25 to maintain a continuous pressure profile or an intermittent pressure profile in the airspace within the suction dome 20.

As shown in FIG. 1, the NPWT unit 12 includes a mobile communication device 36, such as cellular "smart phone." In a preferred embodiment, the mobile communication device 36 includes a microprocessor 38 running an Android or iOS operating system, a touch screen display/interface 40, data storage 42, a battery 43, a data input/output interface 44, a wireless transceiver/modem 46, a global positioning system (GPS) module 48, and a camera 50. The data interface 44 is preferably serial-over-USB protocol (3.3V serial TTL), but could also be Ethernet, SPI, I2C or CAN bus.

Figure 9A:
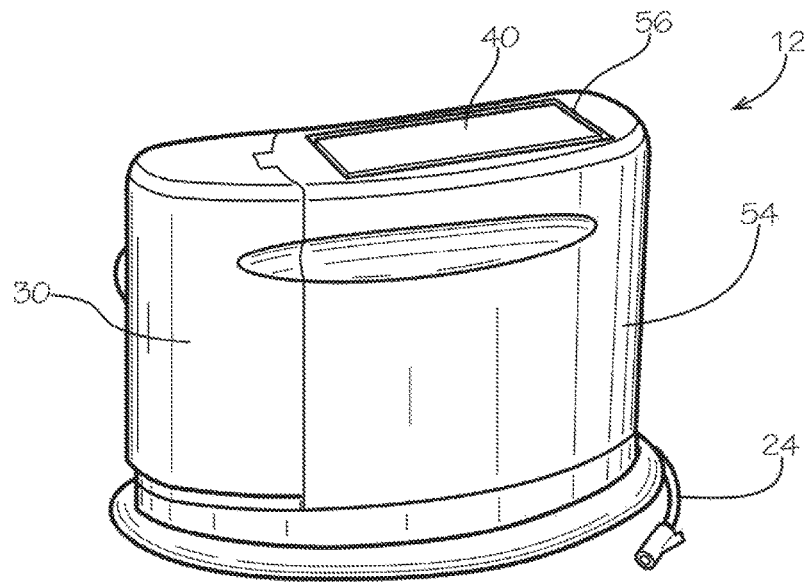
FIGS. 9A and 9B depict a physical configuration of a negative pressure wound therapy unit according to an embodiment of the invention.
Figure 9B:
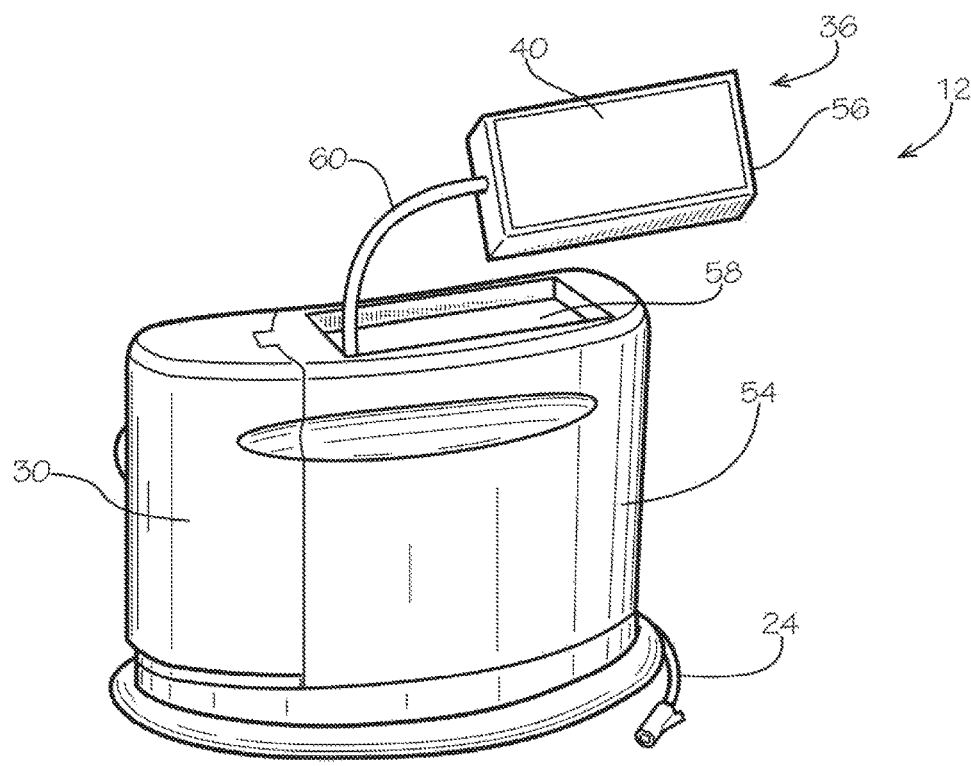

As depicted in FIGS. 9A and 9B, components of the NPWT unit 12 are disposed in or on a NPWT unit housing 54, wherein the fluid canister 30 is attached to one side of the housing 54. In a preferred embodiment, the components of the mobile communication device 36 are disposed within a separate and removable mobile communication device housing 56, wherein the touch screen display/interface 40 is disposed on an upper surface of the housing 56. As shown in FIG. 9A, the mobile communication device housing 56 may be disposed within a recess 58 in the upper surface of the NPWT unit housing 54. In this configuration, the touch screen display/interface 40 is substantially flush with the upper surface of the housing 54. As shown in FIG. 9B, the mobile communication device housing 56 may be removed from the recess 58, with electrical connections between the housing 54 and the housing 56 provided by a tether harness 60. In preferred embodiments, the tether harness 60 provides power and data interface connections between the mobile communication device 36 in the housing 56 and the microcontroller 28 and battery/charging circuit 34 in the housing 54.

In alternative embodiments, when the mobile communication device housing 56 is disposed in the recessed area 58, a microUSB connector on the housing 56 engages a mating connector within the recessed area 58. In these embodiments, the microUSB connector within the recess 58 may be PCB-mounted on an embedded motherboard for the controller 28.

In some embodiments, the housing 56 is hinged with respect to the housing 54. In the hinged configuration, the housing 56 may be flipped up and tilted with respect to the housing 54, such as to provide an advantageous angle for viewing and operating the touch screen display/interface 40.

In the preferred embodiment depicted in FIG. 1, electrical power for the vacuum pump 22 and valve 25 are provided by the battery 34 disposed within the NPWT unit housing 54. The battery 34 also continuously charges the smaller battery 43 that powers the mobile communication device 36. Preferably, the battery 43 powers the embedded controller 28 through the tether harness 60. In preferred embodiments, a power on/off button on the touch screen 40 of the mobile communication device 36 controls power to the unit 12. In this configuration, the embedded controller 28 does not drain the battery 43 when the unit 12 is powered off.

Figure 2:
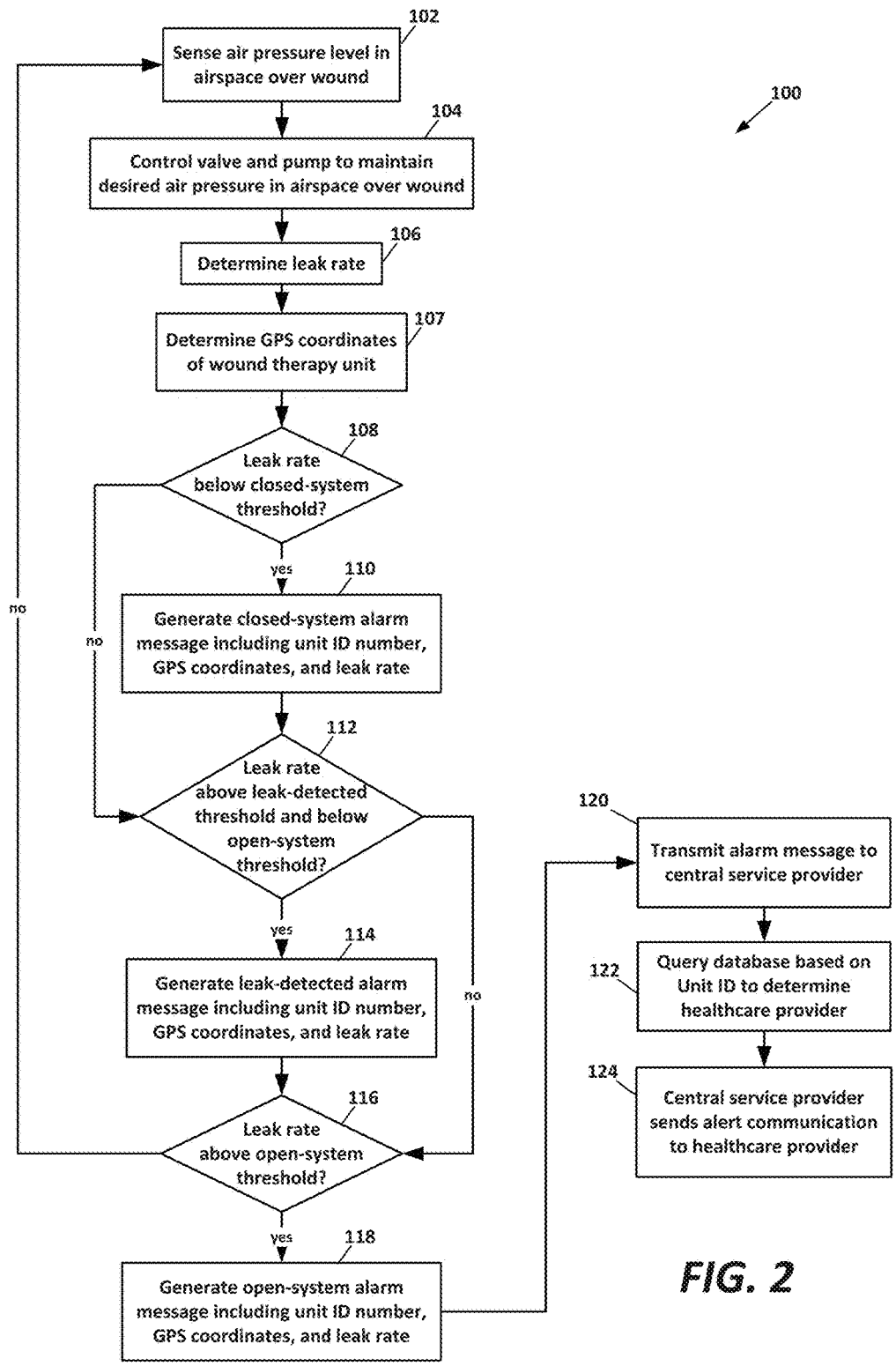
FIGS. 2-8 depict flowcharts of methods for monitoring and controlling a negative pressure wound therapy unit according to embodiments of the invention.

FIG. 2 depicts a process 100 for monitoring and controlling negative pressure wound therapy using the system 10 depicted in FIG. 1. It should be appreciated that the order of many of the process steps shown in FIG. 2 and described herein is not critical to the operation of the system, and the order of the steps may be rearranged in other embodiments of the invention. The pressure sensor 26, which is in fluid communication with the airspace within the suction dome 20, generates a pressure signal based on the sensed air pressure (step 102). The pressure signal is provided to the controller 28, which controls the pump 22 and valve 25 to maintain the pressure level within a desired range as discussed in more detail hereinafter (step 104). The pressure signal is also digitally sampled periodically (such as at 30 second intervals), and the sampled pressure measurements versus time are used to determine the system leak rate that is stored in the data storage device 42 (step 106).

The GPS module 48 periodically generates location coordinate information indicative of the geographic location of the NPWT unit 12 (step 107). For example, this location information may be generated once per hour. The location information is preferably stored in the data storage device 42. In alternative embodiments, location coordinate information may be determined based on cellular telephone network data or Wi-Fi data or combinations of such data with GPS data.

In preferred embodiments, the microcontroller 28 may be set to control the valve 25 and vacuum pump 22 to generate two types of negative air pressure profiles within the suction dome 20: (1) a generally constant pressure over time, or (2) an intermittent pressure profile wherein a first pressure level is maintained during periodic intervals separated by intervals of a second pressure level that is different from the first level (a square wave profile). The constant or intermittent pressure profile is set based on control signals provided by the microprocessor 38 via the data interface 44. The pressure profile is selected either by a manual entry using the touch screen interface 40 or by remote control as described hereinafter.

Regardless of the pressure profile selected, the microprocessor 38 monitors the sampled pressure measurements to determine whether the system leak rate is within certain boundaries. In a preferred embodiment, three leak rate thresholds are defined: (1) a closed-system threshold, (2) leak-detected threshold, and (3) open-system threshold. A leak rate below the closed-system threshold indicates that the dressing on the wound may be sealed too tightly such that air cannot pass through the dressing. A leak rate that is above the open-system threshold indicates that the system is open to the outside air, which may be caused by an open hose connection or an unsealed suction dome. A leak rate that is below the open-system threshold but above the leak-detected threshold indicates there is a leak in the system that is causing a pressure change at a lower rate than may be caused by an open-system problem.

If the microprocessor 38 determines that the leak rate is below the closed system threshold (step 108), the microprocessor 38 generates a closed-system alarm message (step 110). If the microprocessor 38 determines that the leak rate is below the open-system threshold but above the leak-detected threshold (step 112), the microprocessor 38 generates a leak-detected alarm message (step 114). If the microprocessor 38 determines that the leak rate is above the open-system threshold (step 116), the microprocessor 38 generates an open-system alarm message (step 118). All of these alarm messages preferably include at least the unique ID number of the NPWT unit 12, the measured leak rate, an indication of which leak rate condition triggered the alarm, and GPS location information.

The leak rate alarm messages are transmitted by the wireless transceiver 46 via the communication network 16 and are received by the NPWT service provider computer system 14 (step 120). In a preferred embodiment, the leak rate alarm messages are text messages formatted according to Short Messaging Service (SMS) protocol. In other embodiments, the leak rate alarm messages are email messages or other electronically transmitted messages. The NPWT service provider computer system 14 extracts the unique ID number from the leak rate alarm messages and does a database query to identify the particular healthcare provider (such as a particular hospital, medical clinic, DME service provider, etc.) associated with the extracted ID number (step 122).

The NPWT service provider computer system 14 then sends an alert communication via the communication network to the healthcare provider computer 18, such as in the form of an email message (step 124). In this situation, the alert communication preferably includes (1) information to identify the NPWT unit 12 that transmitted the leak rate alarm message or the patient to whom the unit 12 was dispensed, (2) an indication of which leak rate condition triggered the alert, (3) the measured leak rate, and (4) the GPS location coordinates and/or a physical address determined based on the GPS location coordinates. The alert communication may also be received at a mobile device 52 carried by healthcare provider personnel assigned to oversee the treatment of the patient to whom the identified NPWT unit 12 was dispensed. This communication may be via email, text message or other electronic means.

In some embodiments, alert communications may convey a message indicating that a problem with the NPWT unit 12 has been detected and directing the responsible healthcare provider to access the NPWT service provider webpage to view detailed information regarding the problem.

Figure 3:
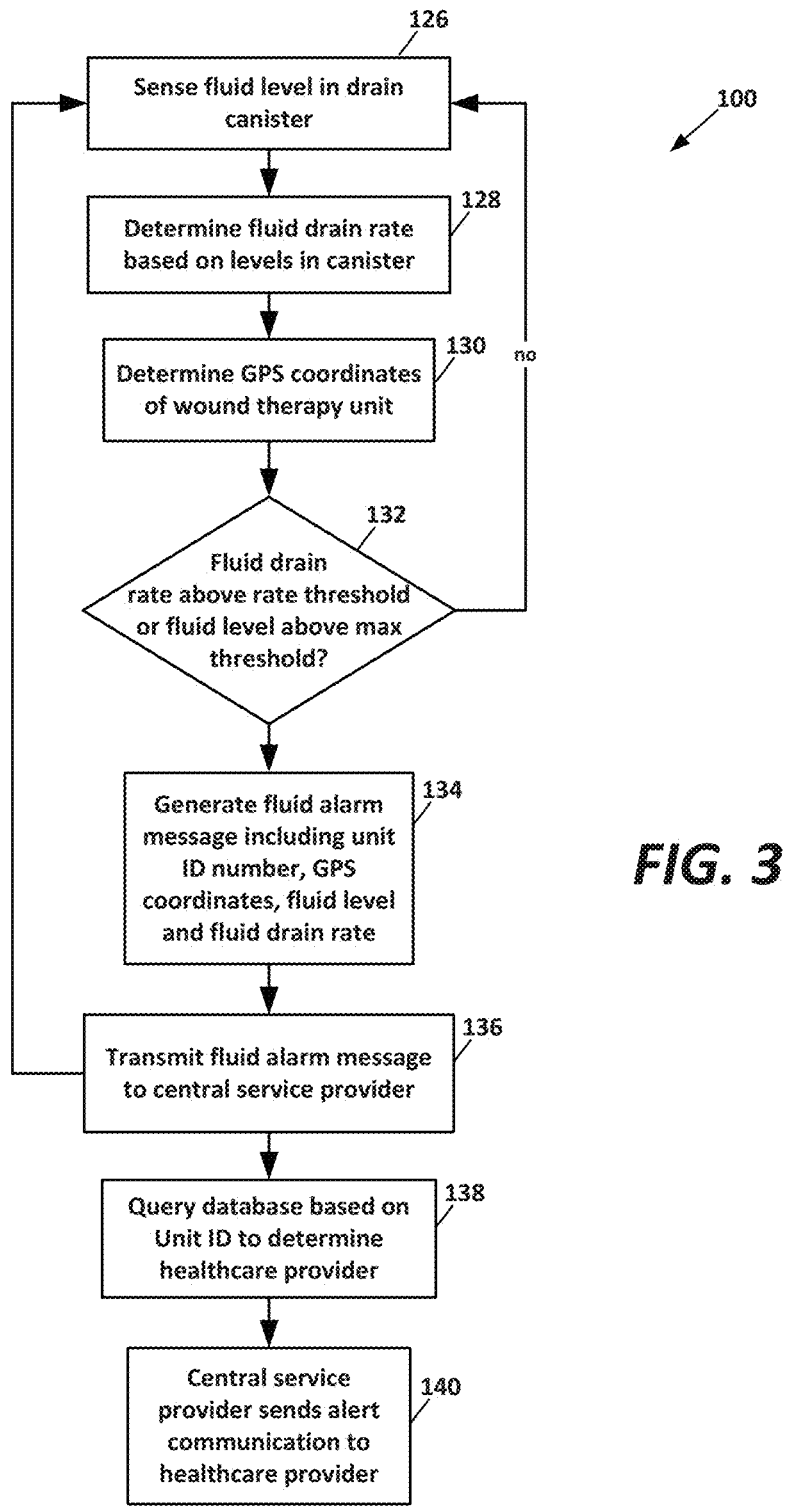

In a preferred embodiment depicted in FIG. 3, the fluid level sensor 32 generates a fluid level signal indicative of the level of the fluid 31 in the canister 30 and the rate of filling of the canister 30, which is related to the drain rate of the wound (step 126). The fluid level signal is also digitally sampled periodically, and the sampled fluid level measurements are transferred via the data interface 44 to be stored in the data storage device 42 as fluid levels (or percentage full) and as a fluid drain rate (step 128).

Based on the fluid drain rate, the microprocessor 38 determines whether the canister 30 is filling with fluid 31 at an abnormally high rate and/or whether the fluid level in the canister has exceeded a maximum threshold (step 132). If the microprocessor 38 determines that the measured fluid level in the canister 30 has risen above a maximum threshold or that the drain rate is abnormally high, the microprocessor 38 generates a fluid alarm message (step 134). Monitoring of the fluid level in the canister helps to prevent exsanguination and contamination of the pump system with overfilled waste.

The fluid alarm message preferably includes at least the unique ID number of the NPWT unit 12, the current fluid level in the canister 30, the fluid drain rate, and GPS location information. The fluid alarm message is transmitted by the wireless transceiver 46 and via the communication network 16 and is received by the NPWT service provider computer system 14 (step 136). In a preferred embodiment, the format of the fluid alarm message is the same as the leak rate alarm message. The NPWT service provider computer system 14 extracts the unique ID number from the fluid alarm message and does a database query to identify the particular healthcare provider associated with the extracted ID number (step 138).

The NPWT service provider computer system 14 then sends an alert communication via the communication network to the healthcare provider computer 18, such as in the form of an email message (step 140). In this situation, the alert communication preferably includes at least (1) information to identify the NPWT unit 12 that transmitted the fluid alarm message or the patient to whom the unit 12 was dispensed, (2) an indication whether a high fluid level or an abnormal drain rate triggered the alert, (3) the fluid level, (4) the fluid drain rate, and (5) the GPS location coordinates and/or a physical address determined based on the GPS location coordinates. The alert communication may also be received at a mobile device 52 carried by healthcare provider personnel assigned to oversee the treatment of the patient to which the identified NPWT unit 12 was dispensed.

Figure 4:
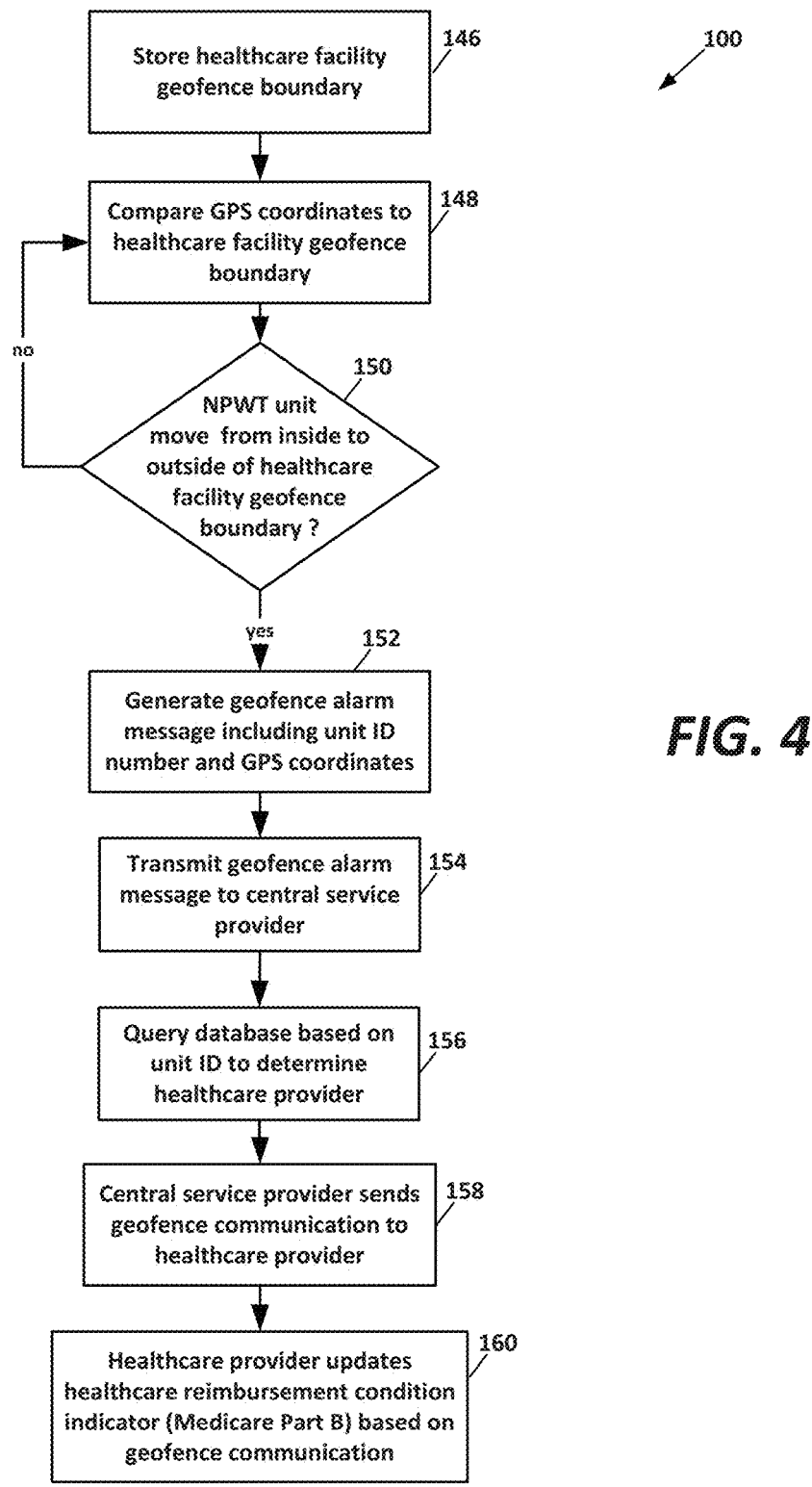

As shown in FIG. 4, GPS information transmitted from the NPWT unit 12 may be used in determining that the NPWT unit 12 has departed from a hospital or other healthcare facility, and this information may be used in determining whether cost reimbursement for the unit should be under Medicare Part A or Part B. As discussed above, the GPS module 48 periodically (such as once per hour) generates location coordinate information indicative of the geographic location of the NPWT unit 12, and the location information is stored in the data storage device 42 (step 107 in FIG. 2; step 130 in FIG. 3).

Also stored in the data storage device 42 is geofence boundary information indicating a geographic boundary around a healthcare facility (step 146). For example, the geofence information may define a circle of a particular radius centered on the healthcare facility. The microprocessor 38 periodically compares the location information determined by the GPS module 48 with the geofence boundary information stored in data storage device 42 (step 148). If the location information indicates that a NPWT unit 12 that was previously inside the geofence boundary has moved outside the geofence boundary (step 150), the microprocessor 38 generates a geofence exit message (step 152).

The geofence exit message preferably includes at least the unique ID number of the NPWT unit 12 and GPS location information. The geofence exit message is transmitted by the wireless transceiver 46 and via the communication network 16 and is received by the NPWT service provider computer system 14 (step 154). In a preferred embodiment, the format of the geofence exit message is the same as the pressure alarm message. The NPWT service provider computer system 14 extracts the unique ID number from the geofence exit message and does a database query to identify the particular healthcare provider associated with the extracted ID number (step 156).

The NPWT service provider computer system 14 sends a geofence alert communication via the communication network to the healthcare provider computer 18, such as in the form of an email message (step 158). In this situation, the geofence alert communication preferably includes at least (1) information to identify the NPWT unit 12 that transmitted the geofence exit message or the patient to whom the unit 12 was dispensed, (2) an indication that a geofence boundary crossing triggered the alert, and (3) the GPS location coordinates and/or a physical address determined based on the GPS location coordinates. The geofence alert communication may also be received at a mobile device 52 carried by healthcare provider personnel assigned to oversee the treatment of the patient to whom the identified NPWT unit 12 was dispensed.

In an alternative embodiment, the geofence boundary information is stored in the database 15 of the NPWT service provider computer system 14. The location information determined by the GPS module 48 is periodically transmitted from the NPWT unit 12 via the communication network 16 to the NPWT service provider computer system 14 that then performs the comparison of the received location information to the geofence boundary to determine if the unit 12 has crossed the boundary (step 148). Upon a boundary crossing event, the NPWT service provider computer system 14 generates and sends the geofence alert communication via the communication network to the healthcare provider computer 18 as described above.

In a preferred embodiment, based on receipt of the geofence alert communication, the healthcare provider computer 18 automatically updates the healthcare provider records to indicate that the cost reimbursement regime for the unit 12 has changed from Medicare Part A to Medicare Part B (step 160). Alternatively, the healthcare provider computer 18 automatically generates an email message (or other message format) directed to a healthcare administrator who is tasked with making a decision regarding whether the Medicare reimbursement regime should be changed for the particular unit 12 that transmitted the geofence alarm message. Also, the insurance reimbursement indicator for the unit may be updated at this time in the NPWT unit database 15 of the service provider computer system 14.

A change in the location of the unit 12 may also be used to trigger the updating of records to indicate the transition of responsibility for the care of the patient from the hospital to a home health care agency or DME caregiver. Such a location change may also prompt a home caregiver to set up the initial appointment for dressing changes and education of the patient. Location monitoring may also be used to locate the unit if it is not returned after the treatment protocol has been completed and to follow-up on any alarms sent back to the caregiver.

In some embodiments, the transition from hospital care to home care may be indicated by a change in the type of container used to collect fluid from the wound. For example, during the patient's stay in the hospital, a larger stand-alone waste container may be r:connected to the unit 12. When it is time for the patient to leave the hospital, the stand-alone waste container is disconnected and the onboard waste canister 31 is installed in the unit 12. This switch-out triggers the billing transition from Medicare Part A to Part B and the transition to home care event scheduling.

Figure 5:
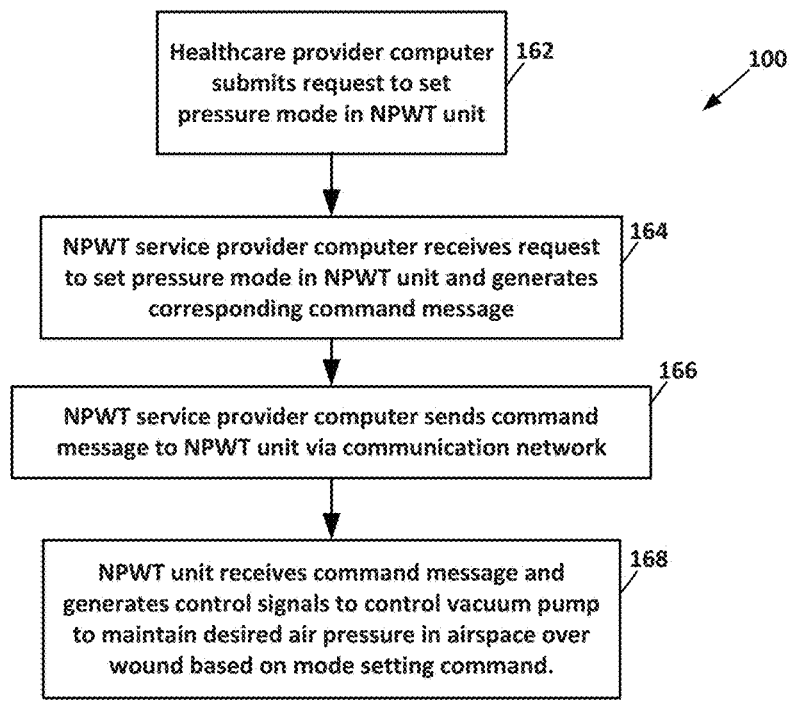

In some embodiments, the NPWT unit 12 may be remotely controlled by the healthcare provider computer 18 via the communication network 16. As depicted in FIG. 5, remote control is initiated when the healthcare provider computer 18 submits a control request to the NPWT service provider computer system 14 (step 162). For example, the control request may be a mode setting request specifying that a particular NPWT unit 12 is to be activated in a continuous pressure mode or an intermittent pressure mode. In this situation, the control request includes the NPWT unit ID number, a mode indicator (continuous or intermittent), a continuous pressure level setting (for continuous mode), a high vacuum pressure setting (for intermittent mode), a high vacuum time interval setting (for intermittent mode), a low vacuum pressure setting (for intermittent mode), and a low vacuum time interval setting (for intermittent mode). The NPWT service provider computer system 14 receives the control request via the communication network 16 and generates a command message based on the contents of the control request (step 164). The NPWT service provider computer system 14 then transmits the command message to the identified NPWT unit 12 via the communication network 16 (step 166). The NPWT unit 12 receives the command message and generates the appropriate control signals to control the vacuum pump 22 and valve 25 to maintain the desired continuous or intermittent negative air pressure in the airspace over the wound (step 168).

The table depicted in FIG. 10 lists various command messages that may be transmitted to the NPWT unit 12 and corresponding response messages generated by the NPWT unit 12, according to a preferred embodiment.

In some embodiments, the data storage device 42 of the mobile communication device 36 stores media for guiding a user in operation of the NPWT unit 12. For example, user guide documentation and demonstration videos may be stored and accessed for viewing on the display screen 40.

Figure 6:
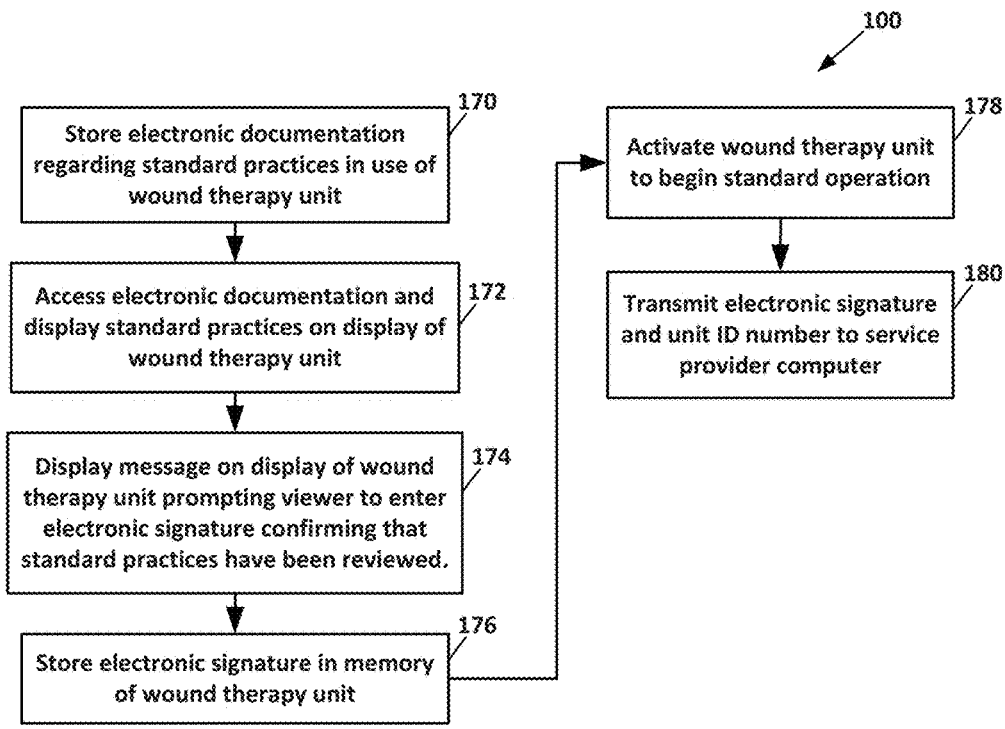

Applicable laws may require that some documentation, such as durable medical equipment (DME) supplier standards, must be reviewed by a user of the NPWT unit 12 and that confirmation of such user review (such as a user signature) must be recorded. FIG. 6 depicts a process implemented by a preferred embodiment of the invention for displaying documentation to a user and recording a user's digital signature. First the electronic documentation is stored in the data storage device 42 of the NPWT unit 12 (step 170), such as during factory programming of the unit 12. Alternatively, the documentation may be stored in the service provider computer system 14 and transmitted to the NPWT unit 12 via the communication network 16 at the appropriate time for viewing by the user. The electronic documentation is retrieved from the data storage device 42 and displayed on the display screen 40 (step 172). This may occur automatically when the unit 12 is initially powered on or after a system reset. A message is also displayed on the display device 40 prompting the user to enter an electronic signature to confirm that the user has read and understands the displayed standard practice disclosure materials (step 174). Once the user's electronic signature has been stored in the data storage device 42 (step 176), the NPWT unit 12 is unlocked to begin controlling negative pressure wound therapy (step 178). In a preferred embodiment, the user's electronic signature and the unique ID number of the NPWT unit 12 are transmitted via the communication network 16 to the NPWT service provider computer system 14 for storage in the database 15 (step 180).

Figure 7:
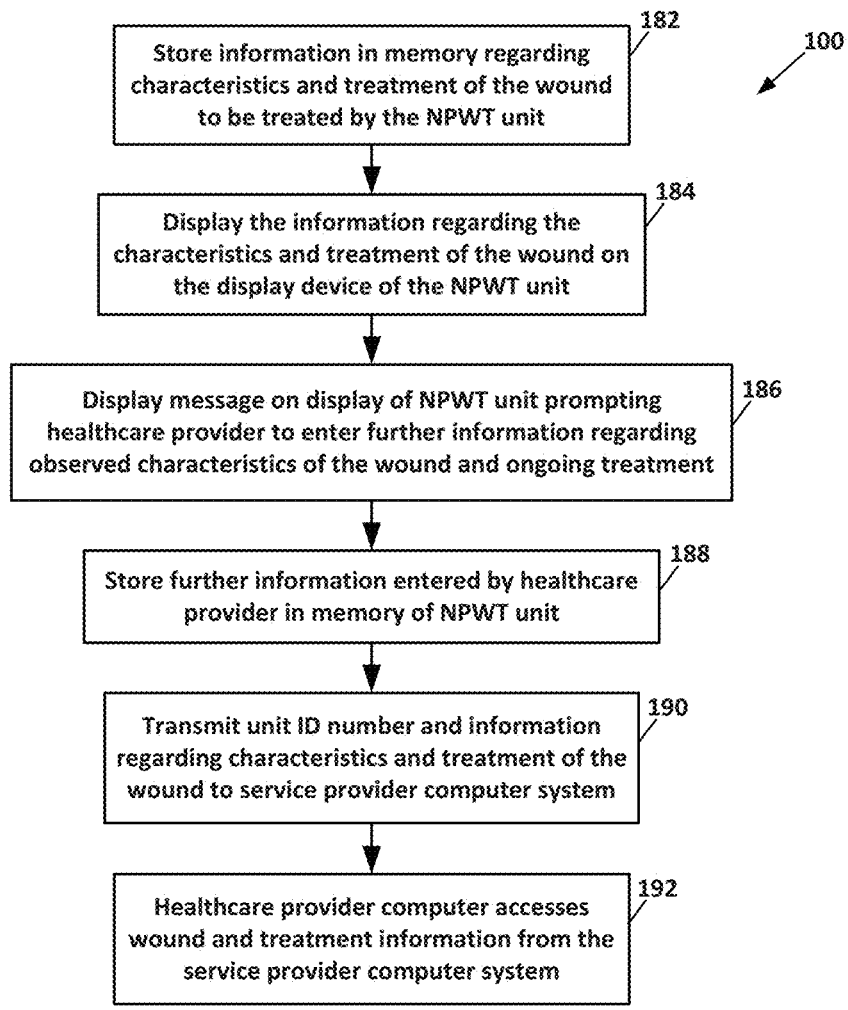

In some preferred embodiments, a doctor or other healthcare provider may store information in the data storage device 42 regarding characteristics of a particular wound being treated and specific instructions for use of the NPWT unit 12 for treatment of the particular wound (FIG. 7, step 182). This information may be recalled and displayed on the display device 40 for reference by the patient or the healthcare provider (step 184). The microprocessor 38 may also generate a prompt that is displayed on the display device 40 asking the healthcare provider to enter further information regarding observed characteristics of the wound and ongoing treatment (step 186). For example, an in-home healthcare provider who is attending to a patient may enter observations regarding the current condition of the wound, any changes that have occurred since a previous visit, and steps taken in further treatment. This information is preferably stored in the data storage device 42 and is transmitted along with the NPWT unit ID number via the communication network 16 to the NPWT service provider computer system 14 to be stored in the database 15 (step 190). This wound characteristic and treatment information may then be accessed by a doctor or other healthcare provider personnel via the communication network 16 (step 192).

Figure 8:
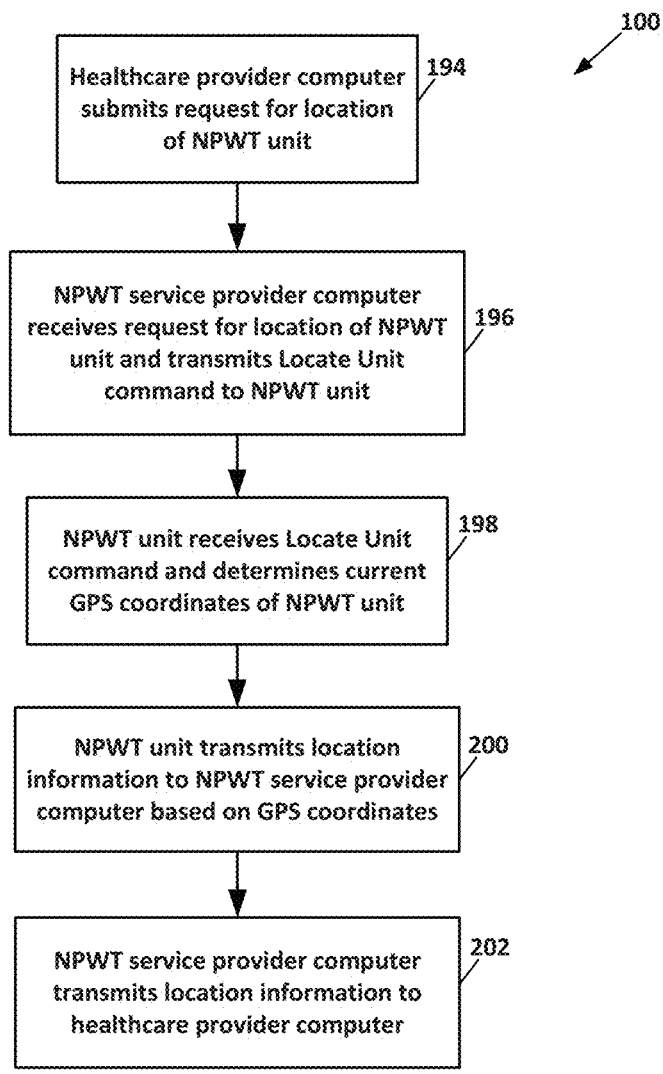

The GPS functionality of the system 10 allows healthcare provider personnel to instantly determine the location of any NPWT unit 12 using the healthcare provider mobile device 52. This function is particularly advantageous in situations in which healthcare provider personnel need to call on a patient to whom an NPWT unit 12 has been dispensed after discharge from the hospital. As shown in FIG. 8, a location request may be submitted from a healthcare provider computer 18 (or a healthcare provider mobile device 52) to the NPWT provider computer system 14 via the communication network 16 (step 194). Upon receipt of the location request, the NPWT provider computer system 14 transmits a "Locate Unit" command to the NPWT unit 12 via the network 16 (step 196). Upon receipt to the Locate Unit command at the NPWT unit 12, the microprocessor 38 queries the GPS module 48 for the current location coordinates of the NPWT unit 12 (step 198). The NPWT unit 12 then transmits the location coordinates (or other location information derived from the location coordinates) to the NPWT service provider computer system 14 via the communication network 16 (step 200). The NPWT service provider computer system 14 sends the location information (GPS coordinates or street address information) to the healthcare provider computer 18 that submitted the location request, such as via an email or text message (step 202). Alternatively, the requested location information may be made available to the healthcare provider by accessing an NPWT service provider website using a browser on the healthcare provider computer 18 (or mobile device 52).

In some embodiments, the mobile communication device 36 of the NPWT unit 12 includes a built-in camera 50 that may be used by the patient or the healthcare provider to record images of the wound and/or the dressing. These images may be transmitted via email or text message from the NPWT unit 12 to the NPWT service provider computer system 14 where they may be accessed by the healthcare provider computer 18. Such images may be used by a doctor or other healthcare provider to remotely evaluate the condition of a wound and the progress of its treatment.

FIG. 11 depicts a listing of global variables used by the operating system of the microprocessor 38 of the NPWT unit 12. These variables are preferably maintained in persistent data storage, even after power loss, and are available in the various operational states of the unit 12.

FIG. 12 depicts a listing of various fixed settings used by the operating system of the microprocessor 38 of the NPWT unit 12.

FIG. 13 depicts a listing of various commands sent by the microprocessor 38 of the mobile communication device 36 to the controller 28 of the NPWT unit 12. Among other things, these commands control the starting and stopping of therapy and performance of diagnostics on the unit 12.

FIG. 14 depicts a listing of various transition states of the microprocessor 38 of the NPWT unit 12.

As discussed above, various aspects of the invention described herein are applicable to DME other than NPWT units. Other DME may include sensors for monitoring parameters relevant to the treatment provided by the DME and a mobile communication device 36 for communicating the monitored parameters. For example, a rehabilitative brace or a range-of-motion brace may include sensors for monitoring the angle of a joint such as a knee, and for monitoring the position of the patient and patient movement to determine compliance with a rehabilitation protocol. Sensors on brace buckles may detect whether and for how long each day that the brace is being worn by the patient.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A system for monitoring and controlling negative pressure wound therapy for treating a wound on a person's body, the system comprising:

means for maintaining reduced air pressure in an airspace over the wound;

a pressure sensor for sensing air pressure and generating a pressure signal based on sensed air pressure;

a microcontroller in electrical communication with the means for maintaining reduced air pressure and the pressure sensor, the microcontroller for controlling the means for maintaining reduced air pressure based at least in part on the pressure signal from the pressure sensor;

a mobile communication device comprising:

a microprocessor in electrical communication with the microcontroller, the microprocessor for executing software instructions to generate control signals that are provided to the microcontroller to control the means for maintaining reduced air pressure to maintain one or more of a continuous reduced air pressure state or an intermittent reduced air pressure state in the airspace over the wound, the microprocessor for executing software instructions to monitor the pressure signal and generate one or more of a closed-system alarm if the pressure signal indicates an air pressure leak rate that is below a closed-system threshold, a leak-detected alarm if the pressure signal indicates an air pressure leak rate that is above a leak-detected threshold and below an open-system threshold, and an open-system alarm if the pressure signal indicates an air pressure leak rate that is above the open-system threshold; and a wireless transceiver in electrical communication with the microprocessor, the wireless transceiver operable to transmit one or more of the pressure signal, the open-system alarm, the leak-detected alarm, and the closed-system alarm via one or more communication networks; and a negative pressure wound treatment service provider computer in communication with the wireless transceiver of the mobile communication device via the one or more communication networks and in communication with a healthcare provider computer via the one or more communication networks, the negative pressure wound treatment service provider computer operable to send an alert communication based on one or more of the pressure signal, the open-system alarm, the leak-detected alarm, and the closed-system alarm to the healthcare provider computer via the one or more communication networks.

2. The system of claim 1 further comprising:

a first housing for enclosing at least a portion of the means for maintaining reduced air pressure and the microcontroller, the first housing having a recess in an outer surface thereof; and a second housing for enclosing the mobile communications device, the second housing sized to fit substantially within the recess in the outer surface of the first housing.

3. The system of claim 2 further comprising a hinged connection between the first housing and the second housing, whereby the second housing is rotatable on the hinged connection to move from a first position in which an outer surface of the second housing is substantially flush with the outer surface of the first housing to a second position in which the outer surface of the second housing is tilted with respect to the outer surface of the first housing.

4. The system of claim 2 further comprising:

a power source disposed in the first housing for providing power to at least the means for maintaining reduced air pressure; and a tether harness connected between the first housing and the second housing through which the mobile communication device in the second housing is in electrical communication with the microcontroller in the first housing.

5. The system of claim 1 further comprising:

a canister for receiving fluid drained from the wound; and a fluid sensor for sensing a quantity of fluid in the canister and generating a fluid signal based thereon, the fluid sensor in electrical communication with the microcontroller, wherein the microcontroller is operable to control the means for maintaining reduced air pressure based at least in part on the fluid signal.

6. The system of claim 5 further comprising:
the microprocessor of the mobile communication device for generating a canister filling rate signal based on the fluid signal;
the wireless transceiver of the mobile communication device for transmitting the canister filling rate signal to the negative pressure wound treatment service provider computer via the communication network; and
the negative pressure wound treatment service provider computer for sending an alert communication based on the canister filling rate signal to the healthcare provider computer via the one or more communication networks.

7. The system of claim 1 wherein the healthcare provider computer is a mobile communication device carried by a healthcare provider assigned to attend to treatment of the person's wound.

8. The system of claim 1 further comprising:
the mobile communication device including a GPS module for generating location coordinate information indicative of the geographic location of the mobile communication device;
the microprocessor of the mobile communication device for determining whether the location coordinate information indicates that the mobile communication device has moved from inside to outside a geofence boundary and for generating a geofence alert message based thereon;
the wireless transceiver of the mobile communication device for transmitting the geofence alert message to the negative pressure wound treatment service provider computer via the one or more communication networks; and
the negative pressure wound treatment service provider computer for sending a geofence alert communication based on the geofence alert message to the healthcare provider computer via the one or more communication networks.

9. The system of claim 1 further comprising:
the mobile communication device including a GPS module for generating location coordinate information indicative of the geographic location of the mobile communication device;
the wireless transceiver of the mobile communication device for transmitting the location coordinate information via the one or more communication networks;
the negative pressure wound treatment service provider computer for determining whether the location coordinate information indicates that the mobile communication device has moved from inside to outside a geofence boundary, and for sending a geofence alert communication to the healthcare provider computer via the one or more communication networks.

10. The system of claim 9 wherein the healthcare provider computer updates a healthcare insurance reimbursement condition indicator based on the geofence alert communication.

11. The system of claim 1 wherein
the mobile communication device further comprises an imaging device for capturing a digital image of the wound, and
the wireless transceiver of the mobile communication device further for transmitting the digital image of the wound to a negative pressure wound treatment service provider.

12. The system of claim 1 further comprising:
the negative pressure wound treatment service provider computer operable to generate a pressure-setting command message and transmit the pressure-setting command message to the mobile communication device via the one or more communication networks;
the wireless transceiver of the mobile communication device for receiving the pressure-setting command message via the one or more communication networks; and
the microprocessor of the mobile communication device for executing software instructions to generate control signals based on the pressure-setting command message, wherein the control signals are provided to the microcontroller to control the means for maintaining reduced air pressure to maintain a reduced air pressure in the airspace over the wound.

13. The system of claim 1 further comprising:
the mobile communication device including a GPS module for determining a geographic location of the mobile communication device after the person whose wound is being treated by the system has been discharged from a healthcare facility;
the microprocessor of the mobile communication device for generating a location message based on the geographic location;
the wireless transceiver of the mobile communication device for transmitting the location message to the negative pressure wound treatment service provider computer via the one or more communication networks; and
the negative pressure wound treatment service provider computer for providing location information via the one or more communication networks to a mobile communication device carried by the healthcare provider, the location information indicating to the healthcare provider a location at which to find the person whose wound is being treated by the system.

14. The system of claim 1 wherein the mobile communication device includes a data storage device that stores an identification number for uniquely identifying the mobile communication device, and wherein the system further comprises:
the negative pressure wound treatment service provider computer receiving from the healthcare provider computer identification information for identifying the person whose wound is being treated by the system;
the microprocessor of the mobile communication device for generating a message that includes the identification number stored in the data storage device of the mobile communication device;
the wireless transceiver of the mobile communication device for transmitting the message that includes the identification number to the negative pressure wound treatment service provider computer via the one or more communication networks; and
the negative pressure wound treatment service provider computer for associating the identification number transmitted from the mobile communication device with the identification information sent from the healthcare provider computer.

15. The system of claim 1 wherein the mobile communication device further comprises:

a data storage device for storing electronic documentation of standard practices with which law requires medical device suppliers to abide and to disclose to persons being treated by the system;

a touch-sensitive display for displaying the standard practices for viewing by the person being treated by the system;

the touch-sensitive display for receiving an indication from the person being treated by the system confirming that the person has viewed the standard practices; and the wireless transceiver further for transmitting the indication to a negative pressure wound treatment service provider computer via the one or more communication networks.

16. The system of claim 1 wherein the mobile communication device further comprises:

a data storage device for storing information regarding characteristics of the wound and treatment of the wound;

a touch-sensitive display for displaying the information regarding characteristics of the wound and treatment of the wound for viewing by the healthcare provider attending to the person being treated by the system;

the touch-sensitive display for receiving information from the healthcare provider regarding characteristics of the wound and treatment of the wound provided to the person by the healthcare provider; and the wireless transceiver further for transmitting information regarding characteristics of the wound and treatment of the wound to a negative pressure wound treatment service provider computer via the one or more communication networks.

17. The system of claim 1 wherein the mobile communication device further comprises:

a touch-sensitive display for displaying a prompt for viewing by the healthcare provider, the prompt requesting input regarding whether use of the system for treatment of the person's wound is covered by a particular type of healthcare insurance;

the touch-sensitive display for receiving information from the healthcare provider in response to the prompt displayed on the display screen; and the wireless transceiver further for transmitting the information input by the healthcare provider to a negative pressure wound treatment service provider computer via the one or more communication networks.

18. The system of claim 1 wherein the means for maintaining reduced pressure in an airspace over the wound comprises:

a vacuum pump in electrical communication with the microcontroller;

a valve in electrical communication with the microcontroller and in fluid communication with the vacuum pump; and a suction dome disposed over the wound and in fluid communication with the valve.

19. A microprocessor-implemented method for maintaining reduced air pressure in an airspace over a wound on a person's body using a negative pressure wound therapy unit, the method comprising:

(a) the negative pressure wound therapy unit sensing air pressure in the airspace over the wound and generating a pressure signal based on sensed air pressure;

(b) the negative pressure wound therapy unit generating control signals to control a vacuum pump in the negative pressure wound therapy unit to maintain a continuous reduced air pressure state or an intermittent reduced air pressure state in the airspace over the wound, the control signals based at least in part on the pressure signal from the pressure sensor;

(c) the negative pressure wound therapy unit generating one or more of a a closed-system alarm if the pressure signal indicates an air pressure leak rate that is below a closed-system threshold, a leak-detected alarm if the pressure signal indicates an air pressure leak rate that is above a leak-detected threshold and below an open-system threshold, and an open-system alarm if the pressure signal indicates an air pressure leak rate that is above the open-system threshold;

(d) the negative pressure wound therapy unit wirelessly transmitting one or more of the pressure signal, the closed-system alarm, the leak-detected alarm, and the open-system alarm from the negative pressure wound therapy unit to a negative pressure wound treatment service provider computer via one or more communication networks; and (e) the negative pressure wound treatment service provider computer sending an alert communication based on one or more of the pressure signal, the closed-system alarm, the leak-detected alarm, and the open-system alarm to a healthcare provider computer via the one or more communication networks.

20. A system for monitoring and controlling negative pressure wound therapy for treating a wound on a person's body, the system comprising:

means for maintaining reduced air pressure in an airspace over the wound;

a canister for receiving fluid drained from the wound;

a fluid sensor for sensing a quantity of fluid in the canister and generating a fluid signal based thereon, the fluid sensor in electrical communication with the microcontroller;

a microcontroller in electrical communication with the means for maintaining reduced air pressure and the fluid sensor, the microcontroller operable to control the means for maintaining reduced air pressure based at least in part on the fluid signal; and a mobile communication device comprising:

a microprocessor in electrical communication with the microcontroller, the microprocessor for generating a canister filling rate signal based on the fluid signal, the microprocessor executing software instructions to generate control signals that are provided to the microcontroller to control the means for maintaining reduced air pressure to maintain one or more of a continuous reduced air pressure state or an intermittent reduced air pressure state in the airspace over the wound;

and a wireless transceiver in electrical communication with the microprocessor;

a negative pressure wound treatment service provider computer in communication with the wireless transceiver of the mobile communication device via one or more communication networks and in communication with a healthcare provider computer via the one or more communication networks;

the wireless transceiver of the mobile communication device for transmitting the canister filling rate signal to the negative pressure wound treatment service provider computer via the communication network; and the negative pressure wound treatment service provider computer for sending an alert communication based on the canister filling rate signal to the healthcare provider computer via the one or more communication networks.

21. A system for monitoring and controlling negative pressure wound therapy for treating a wound on a person's body, the system comprising:
   means for maintaining reduced air pressure in an airspace over the wound;
   a pressure sensor for sensing air pressure and generating a pressure signal based on sensed air pressure;
   a microcontroller in electrical communication with the means for maintaining reduced air pressure and the pressure sensor, the microcontroller for controlling the means for maintaining reduced air pressure based at least in part on the pressure signal from the pressure sensor;
   a first housing for enclosing at least a portion of the means for maintaining reduced air pressure and the microcontroller, the first housing having a recess in an outer surface thereof;
   a mobile communication device comprising:
      a microprocessor in electrical communication with the microcontroller for executing software instructions to generate control signals that are provided to the microcontroller to control the means for maintaining reduced air pressure to maintain one or more of a continuous reduced air pressure state or an intermittent reduced air pressure state in the airspace over the wound;
      a wireless transceiver in electrical communication with the microprocessor; and
   a second housing for enclosing the mobile communications device, the second housing sized to fit substantially within the recess in the outer surface of the first housing.

22. The system of claim 21 further comprising a hinged connection between the first housing and the second housing, whereby the second housing is rotatable on the hinged connection to move from a first position in which an outer surface of the second housing is substantially flush with the outer surface of the first housing to a second position in which the outer surface of the second housing is tilted with respect to the outer surface of the first housing.

23. The system of claim 21 further comprising:
   a power source disposed in the first housing for providing power to at least the means for maintaining reduced air pressure; and
   a tether harness connected between the first housing and the second housing through which the mobile communication device in the second housing is in electrical communication with the microcontroller in the first housing.

24. A system for monitoring and controlling negative pressure wound therapy for treating a wound on a person's body, the system comprising:
   means for maintaining reduced air pressure in an airspace over the wound;
   a pressure sensor for sensing air pressure and generating a pressure signal based on sensed air pressure;
   a canister for receiving fluid drained from the wound;
   a fluid sensor for sensing a quantity of fluid in the canister and generating a fluid signal based thereon,
   a microcontroller in electrical communication with the means for maintaining reduced air pressure, the pressure sensor, and the fluid sensor, the microcontroller for controlling the means for maintaining reduced air pressure based at least in part on the pressure signal from the pressure sensor and the fluid signal from the fluid sensor;
   a mobile communication device comprising:
      a microprocessor in electrical communication with the microcontroller for executing software instructions to generate control signals that are provided to the microcontroller to control the means for maintaining reduced air pressure to maintain one or more of a continuous reduced air pressure state or an intermittent reduced air pressure state in the airspace over the wound, and to generate a canister filling rate signal based on the fluid signal; and
      a wireless transceiver in electrical communication with the microprocessor for transmitting the canister filling rate signal via one or more communication networks; and
   a negative pressure wound treatment service provider computer in communication with the wireless transceiver of the mobile communication device via the one or more communication networks and in communication with a healthcare provider computer via the one or more communication networks, the negative pressure wound treatment service provider computer operable to send an alert communication based on the canister filling rate signal to the healthcare provider computer via the one or more communication networks.

25. A system for monitoring and controlling negative pressure wound therapy for treating a wound on a person's body, the system comprising:
   means for maintaining reduced air pressure in an airspace over the wound;
   a pressure sensor for sensing air pressure and generating a pressure signal based on sensed air pressure;
   a microcontroller in electrical communication with the means for maintaining reduced air pressure and the pressure sensor, the microcontroller for controlling the means for maintaining reduced air pressure based at least in part on the pressure signal from the pressure sensor; and
   a mobile communication device comprising:
      a GPS module in electrical communication with the microprocessor for generating location coordinate information indicative of the geographic location of the mobile communication device; and
      a microprocessor in electrical communication with the microcontroller for executing software instructions to generate control signals that are provided to the microcontroller to control the means for maintaining reduced air pressure to maintain one or more of a continuous reduced air pressure state or an intermittent reduced air pressure state in the airspace over the wound, the microprocessor further operable to execute software instructions to determine whether the location coordinate information indicates that the mobile communication device has moved from inside to outside a geofence boundary and for generating a geofence alert message based thereon; and
      a wireless transceiver in electrical communication with the microprocessor, the wireless transceiver operable to transmit the geofence alert message via one or more communication networks; and
   a negative pressure wound treatment service provider computer in communication with the wireless transceiver of the mobile communication device via one or more communication networks and in communication with a healthcare provider computer via the one or more communication networks, the negative pressure wound treatment service provider computer operable to receive the geofence alert message and to send a geofence alert communication based on the geofence alert message to the healthcare provider computer via the one or more communication networks.

26. A system for monitoring and controlling negative pressure wound therapy for treating a wound on a person's body, the system comprising:
   means for maintaining reduced air pressure in an airspace over the wound;
   a pressure sensor for sensing air pressure and generating a pressure signal based on sensed air pressure;
   a microcontroller in electrical communication with the means for maintaining reduced air pressure and the pressure sensor, the microcontroller for controlling the means for maintaining reduced air pressure based at least in part on the pressure signal from the pressure sensor; and
   a mobile communication device comprising:
      a microprocessor in electrical communication with the microcontroller, the microprocessor operable to execute software instructions to generate control signals that are provided to the microcontroller to control the means for maintaining reduced air pressure to maintain one or more of a continuous reduced air pressure state or an intermittent reduced air pressure state in the airspace over the wound;
      a GPS module in electrical communication with the microprocessor for generating location coordinate information indicative of the geographic location of the mobile communication device; and
      a wireless transceiver in electrical communication with the microprocessor for transmitting the location coordinate information via one or more communication networks; and
   a negative pressure wound treatment service provider computer in communication with the wireless transceiver of the mobile communication device via the one or more communication networks and in communication with a healthcare provider computer via the one or more communication networks, the negative pressure wound treatment service provider computer for determining whether the location coordinate information indicates that the mobile communication device has moved from inside to outside a geofence boundary, and for sending a geofence alert communication to the healthcare provider computer via the one or more communication networks.

27. The system of claim 26 wherein the healthcare provider computer updates a healthcare insurance reimbursement condition indicator based on the geofence alert communication.

28. A system for monitoring and controlling negative pressure wound therapy for treating a wound on a person's body, the system comprising:
   means for maintaining reduced air pressure in an airspace over the wound;
   a pressure sensor for sensing air pressure and generating a pressure signal based on sensed air pressure;
   a microcontroller in electrical communication with the means for maintaining reduced air pressure and the pressure sensor, the microcontroller for controlling the means for maintaining reduced air pressure based at least in part on the pressure signal from the pressure sensor;
   a mobile communication device comprising:
      a data storage device for storing an identification number for uniquely identifying the mobile communication device;
      a microprocessor in electrical communication with the data storage device for executing software instructions to generate control signals that are provided to the microcontroller to control the means for maintaining reduced air pressure to maintain one or more of a continuous reduced air pressure state or an intermittent reduced air pressure state in the airspace over the wound, the microprocessor further operable to generate a message that includes the identification number stored in the data storage device of the mobile communication device; and
      a wireless transceiver in electrical communication with the microprocessor for transmitting the message that includes the identification number via one or more communication networks; and
   a negative pressure wound treatment service provider computer in communication with the wireless transceiver of the mobile communication device via the one or more communication networks and in communication with a healthcare provider computer via the one or more communication networks, the negative pressure wound treatment service provider computer operable to receive from the healthcare provider computer identification information for identifying the person whose wound is being treated by the system, and to associate the identification number transmitted from the mobile communication device with the identification information sent from the healthcare provider computer.

29. A system for monitoring and controlling negative pressure wound therapy for treating a wound on a person's body, the system comprising:
   means for maintaining reduced air pressure in an airspace over the wound;
   a pressure sensor for sensing air pressure and generating a pressure signal based on sensed air pressure;
   a microcontroller in electrical communication with the means for maintaining reduced air pressure and the pressure sensor, the microcontroller for controlling the means for maintaining reduced air pressure based at least in part on the pressure signal from the pressure sensor; and
   a mobile communication device comprising:
      a microprocessor in electrical communication with the microcontroller for executing software instructions to generate control signals that are provided to the microcontroller to control the means for maintaining reduced air pressure to maintain one or more of a continuous reduced air pressure state or an intermittent reduced air pressure state in the airspace over the wound;
      a data storage device in electrical communication with the microprocessor for storing electronic documentation of standard practices with which law requires medical device suppliers to abide and to disclose to persons being treated by the system;
      a touch-sensitive display in electrical communication with the microprocessor for displaying the standard practices for viewing by the person being treated by the system and for receiving an indication from the person being treated by the system confirming that the person has viewed the standard practices; and
      a wireless transceiver in electrical communication with the microprocessor for transmitting the indication to a negative pressure wound treatment service provider computer via the one or more communication networks.

30. A system for monitoring and controlling negative pressure wound therapy for treating a wound on a person's body, the system comprising:
    means for maintaining reduced air pressure in an airspace over the wound;
    a pressure sensor for sensing air pressure and generating a pressure signal based on sensed air pressure;
    a microcontroller in electrical communication with the means for maintaining reduced air pressure and the pressure sensor, the microcontroller for controlling the means for maintaining reduced air pressure based at least in part on the pressure signal from the pressure sensor; and
    a mobile communication device comprising:
        a microprocessor in electrical communication with the microcontroller for executing software instructions to generate control signals that are provided to the microcontroller to control the means for maintaining reduced air pressure to maintain one or more of a continuous reduced air pressure state or an intermittent reduced air pressure state in the airspace over the wound;
        a data storage device in electrical communication with the microprocessor for storing information regarding characteristics of the wound and treatment of the wound;
        a touch-sensitive display in electrical communication with the microprocessor for displaying the information regarding characteristics of the wound and treatment of the wound for viewing by a healthcare provider attending to the person being treated by the system, and for receiving information from the healthcare provider regarding characteristics of the wound and treatment of the wound provided to the person by the healthcare provider; and
        a wireless transceiver in electrical communication with the microprocessor for transmitting information regarding characteristics of the wound and treatment of the wound to a negative pressure wound treatment service provider computer via the one or more communication networks.

31. A system for monitoring and controlling negative pressure wound therapy for treating a wound on a person's body, the system comprising:
    means for maintaining reduced air pressure in an airspace over the wound;
    a pressure sensor for sensing air pressure and generating a pressure signal based on sensed air pressure;
    a microcontroller in electrical communication with the means for maintaining reduced air pressure and the pressure sensor, the microcontroller for controlling the means for maintaining reduced air pressure based at least in part on the pressure signal from the pressure sensor; and
    a mobile communication device comprising:
        a microprocessor in electrical communication with the microcontroller for executing software instructions to generate control signals that are provided to the microcontroller to control the means for maintaining reduced air pressure to maintain one or more of a continuous reduced air pressure state or an intermittent reduced air pressure state in the airspace over the wound;
        a touch-sensitive display in electrical communication with the microprocessor for displaying a prompt for viewing by a healthcare provider, the prompt requesting input regarding whether use of the system for treatment of the person's wound is covered by a particular type of healthcare insurance, the touch-sensitive display further for receiving information from the healthcare provider in response to the prompt displayed on the display screen; and
        a wireless transceiver in electrical communication with the microprocessor transmitting the information input by the healthcare provider to a negative pressure wound treatment service provider computer via the one or more communication networks.

* * * * *